United States Patent
Jansen

(10) Patent No.: US 8,937,085 B2
(45) Date of Patent: Jan. 20, 2015

(54) PHARMACEUTICAL CARRIER COMPOSITION AND PHARMACEUTICAL COMPOSITION

(75) Inventor: Frans Herwig Jansen, Oud-Turnhout (BE)

(73) Assignee: Dafra Pharma N.V., Turnhout (BE)

( * ) Notice: Subject to any disclaimer, the term of this patent is extended or adjusted under 35 U.S.C. 154(b) by 926 days.

(21) Appl. No.: 12/527,149

(22) PCT Filed: Feb. 13, 2008

(86) PCT No.: PCT/EP2008/001093
§ 371 (c)(1),
(2), (4) Date: Sep. 25, 2009

(87) PCT Pub. No.: WO2008/098750
PCT Pub. Date: Aug. 21, 2008

(65) Prior Publication Data
US 2010/0022588 A1   Jan. 28, 2010

(30) Foreign Application Priority Data
Feb. 13, 2007   (WO) ................. PCT/EP2007/001234

(51) Int. Cl.
*A61K 31/335* (2006.01)
*A61K 31/47* (2006.01)
*A61K 31/137* (2006.01)
*A61K 47/26* (2006.01)
*A61K 9/00* (2006.01)
*A61K 47/38* (2006.01)

(52) U.S. Cl.
CPC ............. *A61K 9/0095* (2013.01); *A61K 31/137* (2013.01); *A61K 31/335* (2013.01); *A61K 31/47* (2013.01); *A61K 47/26* (2013.01); *A61K 47/38* (2013.01)
USPC ............ 514/313; 514/452; 514/653; 514/777

(58) Field of Classification Search
CPC . A61K 9/0095; A61K 31/137; A61K 31/335; A61K 31/47; A61K 47/26; A61K 47/38
See application file for complete search history.

(56) References Cited

U.S. PATENT DOCUMENTS

| | | | |
|---|---|---|---|
| 4,499,108 A * | 2/1985 | Sequeira et al. | 514/653 |
| 4,684,666 A * | 8/1987 | Haas | 514/557 |
| 6,214,386 B1 | 4/2001 | Santus et al. | |
| 6,515,008 B1 | 2/2003 | Tiongson et al. | |
| 2004/0237663 A1* | 12/2004 | Farber et al. | 73/861.08 |
| 2006/0198895 A1 | 9/2006 | Kotliar et al. | |
| 2006/0281785 A1* | 12/2006 | Li et al. | 514/313 |
| 2007/0191344 A1* | 8/2007 | Choidas et al. | 514/217.06 |
| 2007/0275962 A1* | 11/2007 | Koul et al. | 514/233.8 |

FOREIGN PATENT DOCUMENTS

| | | |
|---|---|---|
| EP | 1652524 | 5/2006 |
| WO | WO9202217 | 2/1992 |
| WO | WO02069939 | 9/2002 |
| WO | WO2004075817 | 9/2004 |

OTHER PUBLICATIONS

Ansel et al. (Pharmaceutical Dosage Forms and Drug Delivery Systems, 5th ed., Lea & Febiger, 1990).*

* cited by examiner

*Primary Examiner* — Bong-Sook Baek
(74) *Attorney, Agent, or Firm* — Nath, Goldberg & Meyer; Joshua B. Goldberg; Tanya E. Harkins

(57) ABSTRACT

The present invention relates to a pharmaceutical carrier composition and a pharmaceutical composition comprising said pharmaceutical carrier composition. The pharmaceutical composition comprises: (a) at least 20% (w/w) of the composition of a sugar or a sugar alcohol; (b) one or more pharmaceutically acceptable excipients; (c) one or more pharmaceutically active ingredients in their base form; and (d) water up to 100% (w/w). The present pharmaceutical composition is especially resistant against flocculation, clumping and/or precipitation at room temperature during prolonged time-periods such as one or more years.

9 Claims, 1 Drawing Sheet

PHARMACEUTICAL CARRIER COMPOSITION AND PHARMACEUTICAL COMPOSITION

The present invention relates to pharmaceutical carrier compositions and pharmaceutical compositions comprising these pharmaceutical carrier compositions. Especially, the present invention relates to a pharmaceutical compositions mainly comprising a sugar or a sugar alcohol additionally supplemented with one or more pharmaceutically acceptable excipients.

Pharmaceutical compositions comprising active ingredients in the form of organic compounds such small molecules, antibiotics, proteins, nucleic acids and combinations thereof can be administered, for example orally, in the form a liquid formulation or suspension. Such liquid formulation or suspension can be supplied in a ready-to-use form or as dry powder to be reconstituted before use.

If a liquid formulation or suspension is supplied in a ready-to-use form, the constituents can be susceptible to flocculation, clumping and/or precipitation.

The flocculation, clumping and/or precipitation especially occurs when the liquid formulation or suspension is kept at relatively high temperatures and/or during relatively long handling and storing time-periods.

Once flocculated, clumped and/or precipitated, the constituents of the liquid formulation or suspension cannot always be redissolved or reverted to an uniform suspension.

This can result in that the dosage of the active ingredient(s) to be administered is substantially lower than the therapeutically effective dosage intended by the manufacturer or prescribed by the physician.

Especially in third-world regions or during disasters, when professional medical care is scarce, the efficacy of the medical treatment can be, because of this, reduced or even totally absent.

In case of a dry powder to be reconstituted before use, the batch prepared is not always administered immediately after reconstitution. Particularly in third-world regions, the medicament, reconstituted by, for example a physician, is often supplied to a patient to be used in multiple dosages during longer time periods, absent of any medical supervision. For example, for malaria treatment, the medicament is often supplied as a stock solution or suspension, which is then dosed by the patient himself one or more times daily during time periods of one month or more.

When flocculation, clumping and/or precipitation occur(s) during this time period, the concentration of the anti-malaria medicament can become too low to provide an effective treatment although the medication is used by the patient as prescribed.

It is therefore an object of the present invention to address the above described problems associated with liquid formulations or suspensions, especially those liquid formulations or suspensions intended for oral use.

Particularly, it is an object of the present invention to provide a pharmaceutical composition in which flocculation, clumping and/or precipitation is reduced, or even totally absent, even when the pharmaceutical composition is stored at elevated temperatures and/or handled, used or stored during extended time periods.

This object, amongst others, is met by using a pharmaceutical composition, as described in the appended claim 1.

The present inventor has surprisingly discovered that a pharmaceutical composition comprising:

a) at least 20% (w/w) of the composition of a sugar or a sugar alcohol;
b) one or more pharmaceutically acceptable excipients;
c) one or more pharmaceutically active ingredients in their base form; and
d) water up to 100% (w/w)

prevents, or even totally abolishes, flocculation, clumping and/or precipitation of the constituents, and especially the active ingredients in their base form.

It should be noted that the present inventor, when investigating active ingredients in any other form than their base form, such as the addition salts thereof, observed that flocculation, clumping and/or precipitation of the ingredients, and especially the active ingredients, was not prevented. Hence, any other form than the base form of active ingredients is considered not to be encompassed by the present invention.

With respect to constituent (d) according to the present composition, i.e., up to 100% (w/w) water, this also encompasses, within the context of the present invention, any aqueous buffer, such as a phosphate, citrate and/or carbonate buffer, commonly used the pharmaceutical art.

According to a preferred embodiment of the present invention, the pharmaceutical composition comprises at least 25% (w/w) of the composition of a sugar or a sugar alcohol, more preferably 25% to 40% (w/w), and most preferably 30% to 35% (w/w) of the composition of a sugar or a sugar alcohol.

According to the present invention, the sugar or sugar alcohol is preferably a monosaccharide or a disaccharide, preferably chosen from the group consisting of sucrose, glucose, fructose, maltose, lactose, galactose, sorbitol, mannitol, xylitol and malitol.

In an especially preferred embodiment, the sugar is the disaccharide sugar sucrose also designated as saccharose.

The pharmaceutical composition according to the present invention preferably further comprises between 1% to 3% (w/w) of the composition of a cellulose derivative Preferred cellulose derivatives to be used in the present pharmaceutical carrier composition are chosen from the group consisting of microcrystalline cellulose, methyl cellulose, hydroxyethyl cellulose, methylhydroxypropyl cellulose and hydroxypropyl cellulose. Of these cellulose derivatives, methyl cellulose is particularly preferred.

Although the one or more pharmaceutically acceptable excipients of the present carrier composition are excipients commonly used in the pharmaceutical art and known to the skilled person, excipients chosen from the group consisting of citric acid, potassium sorbate, sorbic acid, xanthan gum, guar gum, methyl-p-hydroxy benzoate, propyl-p-hydroxy benzoate, silica, carbomerum, aspertamum, flavor(s) and aromatic substance(s), or any combination thereof, are preferred.

In a particularly preferred embodiment of the present invention, the pharmaceutical composition comprises:

a) between 30% to 35% (w/w) of the composition of sucrose;
b) between 2% and 3% (w/w) of the composition of methyl cellulose;
c) between 0.5% to 2% (w/w) of the composition of one or more excipients;
d) one or more pharmaceutically active ingredients in their base form; and
e) water up to 100% (w/w).

In a preferred embodiment of the present invention, the present pharmaceutical composition comprises between 1% to 5% (w/w), preferably between 2 to 3% (w/w) of the composition of one or more active ingredients in their base form.

Most preferably, the one or more active ingredients in their base form according to the present invention are the base forms of ibuprofen, paracetamol, neuroleptica, antibiotic, amodiaquine, artemether and/or lumefantrine, most preferably amodiaquine, artemether and/or lumefantrine.

The present pharmaceutical composition is, according to a preferred aspect, in dry powder form for providing, upon reconstitution with water up to 100%, the above pharmaceutical composition.

According this aspect, the present pharmaceutical composition is provided as defined above without water or aqueous buffer, but including all other constituents such as the sugar or a sugar alcohol; the one or more pharmaceutically acceptable excipients; and the one or more pharmaceutically active ingredients, all as defined above, in appropriate amounts.

An appropriate amount, as used herein, is an amount which, upon addition of water or an aqueous buffer, provides the above % (w/w) ranges. For example, the present pharmaceutical composition can be obtained by adding approximately 1 part of the dry powder pharmaceutical composition to 2 parts water or aqueous buffer.

Considering the advantageous prevention or inhibition of flocculation, clumping and/or precipitation using the present pharmaceutical composition, the present invention, according yet another aspect, relates to a pharmaceutical carrier composition for providing the present pharmaceutical composition.

Thus, the present invention also relates to pharmaceutical carrier compositions comprising the above constituents in the above % (w/w) ranges except for the one or more pharmaceutically active-ingredients.

The present pharmaceutical composition can suitably be provided by adding the desired amount of the one or more pharmaceutically active ingredients to the pharmaceutical carrier composition.

According to a preferred embodiment of this aspect, the pharmaceutical carrier composition is in dry powder form providing, upon reconstitution with water up to 100% and adding the one or more active ingredients, the present pharmaceutical composition as defined above in appropriate amounts.

An appropriate amount as used herein is an amount which, upon addition of water or an aqueous buffer and the one or more active ingredients, provides the above % (w/w) ranges. For example, the present pharmaceutical composition can be obtained by adding approximately 1 part of the dry powder pharmaceutical carrier composition to 2 parts water or aqueous buffer and adding the one or more active ingredients.

The present invention will be further described using the following preparative examples. The examples are not intended to define the scope of protection of the present invention which is only determined by the appended claims optionally considering the disclosure in the general description and/or examples. In the ezamples, reference us made to the accompanying FIGURE wherein:

FIG. 1: shows an illustrative example of the present pharmaceutical compositions comprising a pharmaceutically active ingredient in its base form (left bottle, amodiaquine base) in comparison with the same pharmaceutical composition wherein the pharmaceutically active ingredient is not in the base form (middle bottle, amodiaquine HCl and right bottle, piperaquine diphosphate).

EXAMPLES

Example 1

Pharmaceutical Composition for an Anti-Malaria Medicament in the Form of a Suspension Materials

| | |
|---|---|
| Sucrose: | YME Kuiper BV, the Netherlands; |
| Avicel CL 611: | FMC Bio Polymer, Wallingtown, Ireland; |
| Citric Acid: | Boom, Meppel, the Netherlands, or JBZ; |
| Xantham gum: | Brenntag Nederland BV, Dordrecht, the Netherlands, or Keltrol T, CP Kelco; |
| Coconut flavor: | Buteressence, Zaandam, the Netherlands; |
| Silicium colloidal anhydrous: | Degussa Nederland BV, Amsterdam, the Netherlands; |
| Methyl-p-hydroxy benzoate*: | Bufa BV, Uitgeest, the Netherlands, or Ueno; |
| Propyl-p-hydroxy benzoate*: | Bufa BV, Uitgeest, the Netherlands. |

*or instead of Methyl-p-hydroxy benzoate and propyl-p-nydroxy benzoate, potassium sorbate and sorbic acid.

Composition and Formulation

| Ingredients | mg | Quality reference |
|---|---|---|
| Active substances | | |
| beta-artemether (base) | 180 | Int. Ph. |
| Lumefantrine (base) | 1080 | Internal monograph (based on Eur. Ph.) |
| Excipients | | |
| Sucrose | 19703 | Eur. Ph. |
| Avicel CL 611 | 1350 | Eur. Ph. |
| Citric acid | 59 | Eur. Ph. |
| Xanthan gum | 120 | Eur. Ph. |
| Methyl-p-hydroxy benzoate* | 48 | Eur. Ph. |
| Propyl-p-hydroxy benzoate* | 12 | Eur. Ph. |
| Coconut flavor | 180 | Eur. food grade |
| Silicium colloidal anhydrous | 67.5 | Eur. Ph. |

*or instead of Methyl-p-hydroxy benzoate and propyl-p-hydroxy benzoate, potassium sorbate and sorbic acid.

Manufacturing Procedure

The industrial production method and operational conditions will be described for a production unit with a capacity of 6666 vials of 60 ml Co-Artesiane.

| Ingredients | Quantity (grams) |
|---|---|
| beta-artemether (base) | 1200 |
| Lumefantrine (base) | 7200 |
| Sucrose | 131340 |
| Avicel CL 611 | 9000 |
| Citric acid monohydrate | 393 |
| Xanthan gum | 800 |
| Methyl-p-hydroxy benzoate* | 320 |
| Propyl-p-hydroxy benzoate* | 80 |
| Coconut flavor | 1200 |
| Silica colloidalis anhydrum | 450 |

*or instead of Methyl-p-hydroxy benzoate and propyl-p-hydroxy benzoate, potassium sorbate and sorbic acid.

Before starting the production, the identity of all constituents is checked. All work is carried out taking into account the regulations of good manufacturing practice. All ingredients are sieved and weighed before mixing.

The ingredients are mixed in the following order in a two different mixers for about in totally 65 minutes±30 seconds.

A premix is prepared in the following order: first a part of the Avicel CL 611, coconut flavor, beta-artemether, citric acid monohydrate, lumefantrine, xanthan gum, methyl-p-hydroxy benzoate and propyl-p-hydroxy benzoate are mixed in a Stephan mixer during different times and at different speeds (in total: 120 sec).

To this first mixing, the second part of Avicel CL 611 is added, thoroughly mixed during 120 sec and transferred into an inox container for transport to the final addition of sucrose in the De Graaf mixing device.

In a second step, a part of the sucrose is transferred to a de Graaf mixer, followed by the premix and the remainder of the sucrose. Finally, colloidal anhydrous silica is added and mixed for 120 minutes.

After final mixing the vials are filled with powder and closed with a stopper, developed to be safe for children. After labeling, the filled vials are packed in a cardboard box together with a leaflet.

To the above vials 60 ml of water is added to provide an effective anti-malaria medicament for oral use. The suspension obtained is stable at room temperature for years and does not show signs of flocculation, clumping and/or precipitation. Because of this, the active ingredients remain uniformly distributed thereby providing an uniform dosage regime to a malaria patient even in absence of trained medical personnel or storage facilities such as a refrigerator.

Example 2

Pharmaceutical Composition for an Anti-Malaria Medicament in the Form of a Suspension Composition and Formulation

| Ingredients | mg | Quality reference |
|---|---|---|
| Active substances | | |
| beta-artemether (base) | 180 | Int. Ph. |
| Lumefantrine (base) | 1080 | Internal monograph (based on Eur.Ph.) |
| Excipients | | |
| Sucrose | 39406 | Eur. Ph. |
| Avicel CL 611 | 2700 | Eur. Ph. |
| Citric acid | 118 | Eur. Ph. |
| Xanthan gum | 240 | Eur. Ph. |
| Methyl-p-hydroxy benzoate* | 96 | Eur. Ph. |
| Propyl-p-hydroxy benzoate* | 24 | Eur. Ph. |
| Coconut flavor | 360 | Eur. food grade |
| Silicium colloidal anhydrous | 135 | Eur. Ph. |

*or instead of Methyl-p-hydroxy benzoate and propyl-p-hydroxy benzoate, potassium sorbate and sorbic acid.

The industrial production method and operational conditions are similar as in example 1 except that 3333 vials of 120 ml Co-Artesiane were produced.

To the above vials, 120 ml of water is added to provide an effective anti-malaria medicament for oral use. The suspension obtained is stable at room temperature for years and does not show signs of flocculation, clumping and/or precipitation. Because of this, the active ingredients remain uniformly distributed thereby providing an uniform dosage regime to a malaria patient even in absence of trained medical personnel or storage facilities such as a refrigerator.

Example 3

Pharmaceutical Composition for an Anti-Malaria Medicament in the Form of a Suspension Materials

| | |
|---|---|
| Sucrose: | YME Kuiper BV, the Netherlands; |
| Avicel CL 611: | FMC Bio Polymer, Wallingtown, Ireland; |
| Citric Acid: | Boom, Meppel, the Netherlands, or JBZ; |
| Xantham gum: | Brenntag Nederland BV, Dordrecht, the Netherlands, or Keltrol T, CP Kelco; |
| Silicium colloidal anhydrous: | Degussa Nederland BV, Amsterdam, the Netherlands; |
| Methyl-p-hydroxy benzoate*: | Bufa BV, Uitgeest, the Netherlands; |
| Propyl-p-hydroxy benzoate*: | Bufa BV, Uitgeest, the Netherlands, or Ueno. |

*or instead of Methyl-p-hydroxy benzoate and propyl-p-hydroxy benzoate, potassium sorbate and sorbic acid.

Composition and Formulation

| Ingredients | mg | Quality reference |
|---|---|---|
| Active substances | | |
| artemether (base) | 150 | Int. Ph. |
| Piperaquine (base) | 1200 | Eur. Ph. |
| Excipients | | |
| Sucrose | 14778 | Eur. Ph. |
| Avicel CL 611 | 2250 | Eur. Ph. |
| Citric acid | 49 | Eur. Ph. |
| Xanthan gum | 200 | Eur. Ph. |
| Methyl-p-hydroxy benzoate* | 40 | Eur. Ph. |
| Propyl-p-hydroxy benzoate* | 10 | Eur. Ph. |
| Citric flavor | 150 | Eur. food grade |
| Carbomerum | 100 | Eur. Ph. |
| Aspertamum | 3 | Eur. Ph. |
| Silicium colloidal anhydrous | 56 | Eur. Ph. |

*or instead of Methyl-p-hydroxy benzoate and propyl-p-hydroxy benzoate, potassium sorbate and sorbic acid.

Manufacturing Procedure

The industrial production method and operational conditions for a production unit with a capacity of 6666 vials of 60 ml are essentially as described in example 1.

Briefly, before starting the production, the identity of all constituents is checked. All work is carried out taking into account the regulations of good manufacturing practice. All ingredients are sieved and weighed before mixing.

The ingredients are mixed in the following order in a two different mixers for about in totally 65 minutes±30 seconds.

A premix is prepared in the following order: first a part of the Avicel CL 611, citric flavor, artemether, citric acid monohydrate, xanthan gum, methyl-p-hydroxy benzoate, propyl-p-hydroxy benzoate, piperaquine phosphate, carbomerum and aspertamum are mixed in a Stephan mixer during different times and at different speeds (in total: 120 sec).

To this first mixing, the second part of Avicel CL 611 is added, thoroughly mixed during 120 sec and transferred into an inox container for transport to the final addition of sucrose in the De Graaf mixing device.

In a second step, a part of the sucrose is transferred to a de Graaf mixer, followed by the premix and the remainder of the sucrose. Finally, colloidal anhydrous silica is added and mixed for 120 minutes.

After final mixing the vials are filled with powder and closed with a stopper, developed to be safe for children. After labeling, the filled vials are packed in a cardboard box together with a leaflet.

To the above vials 60 ml of water is added to provide an effective anti-malaria medicament for oral use. The suspension obtained is stable at room temperature for years and does not show signs of flocculation, clumping and/or precipitation. Because of this, the active ingredients remain uniformly distributed thereby providing an uniform dosage regime to a malaria patient even in absence of trained medical personnel or storage facilities such as a refrigerator.

Comparative Example

The pharmaceutical composition as described in example 3 was prepared but instead of artemether (base) and piperaquine (base) as active ingredients, three compositions comprising amodiaquine base, amodiaquine HCl and piperaquine diphosphate were prepared.

After adding water (60 ml/vial), vials were allowed to stand at room temperature for 48 hours after which a photograph was taken of the vials as shown in FIG. 1.

As is shown in FIG. 1, the pharmaceutical composition in the left vial comprising the amodiaquine base is still a suspension while the pharmaceutical composition comprising amodiaquine HCl (middle vial) and piperaquine diphosphate (right) vial are clearly sedimented.

The invention claimed is:

1. A pharmaceutical composition in the form of a suspension comprising: a) sucrose of not less than 20% (w/w) and not more than 35% (w/w) of the composition; b) one or more pharmaceutically acceptable excipients; c) one or more pharmaceutically active ingredients in their base form in the amount of not less than 1% and not more than 5% (w/w) of the composition, the one or more pharmaceutically active ingredient being selected from the group consisting of arthemether, amodiaquine, lumefantrine and piperaquine; and d) water up to 100% (w/w).

2. The pharmaceutical composition according to claim 1, wherein the amount of the sucrose is not less than 25% and not more than 35% (w/w) of the composition.

3. The pharmaceutical composition according to claim 1, wherein the amount of the sucrose is not less than 30% and not more than 35% (w/w) of the composition.

4. The pharmaceutical composition according to claim 1, further comprising a cellulose derivative of not less than 1% and not more than 3% (w/w) of the composition.

5. The pharmaceutical composition according to claim 4, wherein the cellulose derivative is selected from the group consisting of microcrystalline cellulose, hydroxyl ethyl cellulose, methylhydroxypropyl cellulose and hydroxypropyl cellulose.

6. The pharmaceutical composition according to claim 4, wherein the cellulose derivative is methyl cellulose.

7. The pharmaceutical composition according to claim 1, wherein the one or more pharmaceutically acceptable excipients is selected from the group consisting of citric acid, xanthan gum, guar gum, methyl-p-hydroxy benzoate, propyl-p-hydroxy benzoate, sorbic acid, potassium sorbate and silica.

8. The pharmaceutical composition according to claim 3, comprising: a) sucrose of not less than 30% and not more than 35% (w/w) of the composition; b) one or more pharmaceutically acceptable excipients comprising methyl cellulose of not less than 2% and not more than 3% (w/w) of the composition; c) one or more other excipients of not less than 0.5% and not more than 2% (w/w) of the composition; d) one or more pharmaceutically active ingredients in their base form selected from the group consisting of arthemether, amodiaquine, lumefantrine and piperaquine; and e) water up to 100% (w/w).

9. The pharmaceutical composition according to claim 8, wherein the one or more active ingredients in their base form are present in an amount not less than 2% and not more than 3% (w/w) of the composition.

* * * * *